United States Patent
Bellock et al.

(10) Patent No.: US 9,993,173 B2
(45) Date of Patent: Jun. 12, 2018

(54) ANALYSIS OF ECG DATA FOR ARRHYTHMIA

(71) Applicant: BIOTRONIK SE & Co. KG, Berlin (DE)

(72) Inventors: Steven Bellock, Wilsonville, OR (US); R. Hollis Whittington, Portlanfd, OR (US); Garth Garner, Tigard, OR (US)

(73) Assignee: BIOTRONIK SE & Co. KG (DE)

(*) Notice: Subject to any disclaimer, the term of this patent is extended or adjusted under 35 U.S.C. 154(b) by 8 days.

(21) Appl. No.: 15/256,850

(22) Filed: Sep. 6, 2016

(65) Prior Publication Data
US 2017/0086697 A1    Mar. 30, 2017

Related U.S. Application Data

(60) Provisional application No. 62/234,700, filed on Sep. 30, 2015.

(51) Int. Cl.
| | | |
|---|---|---|
| *A61B 5/04* | (2006.01) | |
| *A61B 5/0468* | (2006.01) | |
| *A61B 5/042* | (2006.01) | |
| *A61B 5/0432* | (2006.01) | |

(52) U.S. Cl.
CPC ........ *A61B 5/0468* (2013.01); *A61B 5/04012* (2013.01); *A61B 5/0422* (2013.01); *A61B 5/0432* (2013.01)

(58) Field of Classification Search
CPC . A61B 5/04012; A61B 5/0422; A61B 5/0432; A61B 5/0468
See application file for complete search history.

(56) References Cited

U.S. PATENT DOCUMENTS

| | | | |
|---|---|---|---|
| 6,487,442 B1* | 11/2002 | Wood | A61B 5/0468 600/515 |
| 6,496,722 B1* | 12/2002 | Schmidt | A61B 5/0468 600/513 |
| 6,671,548 B1 | 12/2003 | Mouchawar et al. | |
| 7,580,748 B2 | 8/2009 | Garner et al. | |
| 7,583,996 B2 | 9/2009 | Lian et al. | |
| 7,899,520 B2 | 3/2011 | Lian et al. | |
| 7,970,462 B2 | 6/2011 | Lefkov et al. | |
| 8,060,198 B2 | 11/2011 | Lian et al. | |
| 8,090,434 B2 | 1/2012 | Lian et al. | |
| 8,265,741 B2 | 9/2012 | Whittington et al. | |
| 8,380,307 B2 | 2/2013 | Lian et al. | |
| 8,396,538 B2 | 3/2013 | Garner et al. | |

(Continued)

OTHER PUBLICATIONS

European Search Report, Application No. 16188684.1, dated Mar. 21, 2017.

*Primary Examiner* — George Manuel
(74) *Attorney, Agent, or Firm* — Craig A. Fieschko, Esq.; DeWitt Ross & Stevens S.C.

(57) ABSTRACT

ECG data is analyzed by detecting points in the ECG data which represent ventricular activity; measuring time intervals between each two consecutive points in the ECG data which represent ventricular activity; and then within a set of such time intervals, evaluating the time intervals by computing at least one comparative dimension for at least one time interval subset. The time interval subset includes at least two time intervals, and the comparative dimension represents variations between the interval lengths between the time intervals of the time interval subset.

18 Claims, 8 Drawing Sheets

(56) References Cited

U.S. PATENT DOCUMENTS

| | | |
|---|---|---|
| 9,020,584 B2 | 4/2015 | Moulder et al. |
| 9,295,428 B2 | 3/2016 | Lian et al. |
| 9,381,365 B2 | 7/2016 | Kibler et al. |
| 2002/0177784 A1 | 11/2002 | Shekhar |
| 2009/0088655 A1* | 4/2009 | Vajdic ................ A61B 5/04011 600/523 |
| 2010/0292596 A1 | 11/2010 | Moulder et al. |
| 2010/0317979 A1 | 12/2010 | Kelly |
| 2011/0130669 A1 | 6/2011 | Garner et al. |
| 2012/0238892 A1 | 9/2012 | Sarkar |
| 2014/0088399 A1 | 3/2014 | Lian et al. |
| 2014/0222110 A1 | 8/2014 | Kibler et al. |
| 2014/0236032 A1 | 8/2014 | Garner et al. |
| 2014/0236034 A1 | 8/2014 | Moulder et al. |
| 2015/0245779 A1 | 9/2015 | Garner et al. |
| 2015/0367135 A1 | 12/2015 | Whittington et al. |
| 2016/0213919 A1 | 7/2016 | Suwito et al. |

\* cited by examiner

ANALYSIS OF ECG DATA FOR ARRHYTHMIA

CROSS-REFERENCE TO RELATED APPLICATIONS

This application claims priority under 35 USC § 119(e) to U.S. Provisional Patent Application 62/234,700 filed 30 Sep. 2015, the entirety of which is incorporated by reference herein.

FIELD OF THE INVENTION

The invention generally relates to implantable cardiac devices, including monitoring devices, pacemakers, defibrillators and cardioverters, which monitor, detect and classify cardiac events, for example atrial tachyarrhythmias. Exemplary versions of the invention more particularly relate to a method and device for detecting atrial fibrillation by evaluating ventricular signals.

BACKGROUND OF THE INVENTION

Some heart rhythm disorders (arrhythmias) are life-threatening and require immediate attention and treatment, such as ventricular fibrillation. Other arrhythmias may require treatment, and/or may be symptomatic of other underlying conditions requiring treatment, but are typically not immediately life-threatening. Atrial fibrillation (AF), for example, is a relatively common cardiac arrhythmia which is associated with increased risk of stroke and death, but which is typically not an immediate threat. Other less-common cardiac arrhythmias that would be beneficial to diagnose include, but are not limited to, paroxysmal ventricular tachycardia, paroxysmal atrial tachycardia, supra ventricular tachycardia, and sinus tachycardia. Although the following discussion will refer to AF for simplicity, it should be understood that the invention is also generally applicable to other cardiac arrhythmias.

AF can be either symptomatic or asymptomatic, and can be paroxysmal or persistent. AF is usually diagnosed when a patient exhibits associated symptoms or complications, such as palpations, congestive heart failure, or stroke. AF may also be diagnosed incidentally during a routine medical evaluation. Patients with asymptomatic paroxysmal AF may have heightened risk of devastating consequences such as stroke, congestive heart failure, or tachycardia-mediated cardiomyopathy for years before a definitive diagnosis of AF is made.

In the field of automated detection of dangerous arrhythmias, several methods for detecting atrial tachyarrhythmias have previously been proposed. It is known to use a so called "X-out-of-Y" criterion to detect an ongoing atrial tachyarrhythmia. U.S. Pat. No. 6,671,548 B1, for example, describes use of such an "X-out-of-Y" criterion wherein an atrial tachyarrhythmia is detected when X number of intervals among the most recent Y number of atrial intervals are found to be shorter than an interval limit corresponding to the tachyarrhythmia rate limit. The numbers X and Y, and the tachyarrhythmia rate limit, may be pre-defined or programmable. The use of the "X-out-of-Y" criterion accommodates for undersensing of some of the atrial events.

A problem in the detection of dangerous arrhythmias from heart activity data such as electrocardiogram (ECG) data is that a generally healthy heart may often exhibit some variability in the ECG data that can confuse or mislead automated detection algorithms. Relatively benign variability may include premature atrial contraction, premature ventricular contraction, and normal sinus arrhythmia. Common types of arrhythmia due to premature ventricular contractions are, for example, continuous alternations of long and short heartbeats with an inherent regularity, which are called bigeminy, trigeminy, and so forth according to the number of ventricular contractions. A major problem with screening for potentially dangerous heart rhythm irregularities, such as atrial fibrillation, ventricular tachycardia, and the like, is that existing detection methods lack sufficient specificity, meaning that existing detection methods are not able to sufficiently differentiate dangerous cardiac arrhythmias from benign arrhythmias. Such existing detection methods produce a high rate of false positives, generating incorrect diagnosis, anxiety in healthy subjects, causing expensive technician review, and possibly spurring unnecessary, expensive, potentially uncomfortable, and inconvenient additional testing.

SUMMARY OF THE INVENTION

The invention seeks to correctly detect and differentiate between life-threatening cardiac arrhythmias (such as AF) from arrhythmias due to periodic premature events, such as bigeminy, trigeminy, and other periodic rhythms.

An exemplary version of the invention involves a method for analyzing ECG data having the steps of:

detecting points in the ECG data which represent ventricular activity, measuring time intervals between each two consecutive points in the ECG data which represent ventricular activity, and evaluating the time intervals within a set of time intervals by computing at least one comparative dimension for at least one time interval subset, wherein the time interval subset includes at least two time intervals. The comparative dimension represents similarity in the interval lengths of the time intervals of the time interval subset. A fixed number N of time intervals lies between each two time intervals of the time interval subset, wherein N is preferably greater than or equal to 1.

For example, the set of time intervals may include at least three time intervals. Also, the points in the ECG data which represent ventricular activity may be QRS complexes, in particular, R-waves.

An additional comparative dimension for at least one time interval subset may be computed for which N=0 within the set of time intervals, that is, the comparative dimension is determined for adjacent time intervals.

Preferably, the comparative dimension is computed by generation of at least a difference, a sum, a ratio, a product, a mean value, a deviation, or a variance.

Preferably, all computed comparative dimensions with equal N are considered as a group within the set of time intervals, and for each group, a count is calculated for those comparative dimensions which fulfill an instability criterion.

Furthermore, each calculated count may be compared with at least one threshold respectively, and the set of time intervals is regarded as irregular when at least one calculated count exceeds at least one threshold respectively, or when all calculated counts exceed at least one threshold respectively.

Preferably, a quality measure (a value or label) is assigned to at least a part of the ECG data when a count of consecutive sets of time intervals which are regarded as irregular exceeds a value A, and/or when within a totality X of sets of time intervals, the count of consecutive sets of time intervals which are regarded as irregular exceeds the value A. For example, the involved time intervals may be tagged (associated with) a pathology indicator, that is, data indicating pathological heart behavior, if the value A is exceeded.

The quality measure assignment to at least a part of the ECG data may be terminated when a count of consecutive sets of time intervals which are regarded as not irregular exceeds a value B, and/or when within a totality Y of sets of time intervals, the count of consecutive sets of time intervals which are regarded as not irregular exceeds the value B.

For instance, the quality measure assignment can include marking the respective ECG data as being indicative of a cardiac arrhythmia, which can typically be identified on the ECG by irregular ventricular activity, for example AF or atrial flutter.

Preferably, the instability criterion is fulfilled when the comparative dimension exceeds a limit. The limit can also be calculated dynamically according to the computed comparative dimensions.

Preferably, the inventive method is employed in a device for analyzing ECG data during the detection phase for a cardiac arrhythmia as AF. The method can also be applied in the initial phase for confirmation of a cardiac arrhythmia within such devices.

The invention also seeks to provide a device for monitoring the heart activity of a living being, for example an implantable cardiac device, such as a monitoring device, especially a monitoring device without atrial electrodes. However, the device could be a pacemaker, a defibrillator or a cardioverter for evaluating cardiac events such as ventricular signals. The device preferably includes:

at least two electrodes for recording a signal which represents the heart activity, a power supply, a memory unit for storing the heart activity signal, and a signal evaluation unit, which is configured for detecting ventricular activity in the signal, measuring time intervals between each two consecutive ventricular activities, and evaluating the time intervals within a set of time intervals. The evaluation of time intervals within a set of time intervals can be performed by computing at least one comparative dimension for at least one time interval subset, wherein:

the time interval subset includes at least two time intervals, the comparative dimension represents the similarity of the interval lengths of the time intervals of the time interval subset, and a fixed number M of time intervals lies between each two time intervals of the time interval subset, and wherein M is preferably greater than or equal to 1.

For example, the set of time intervals can include at least three time intervals. Also, the ventricular activity in the signal can be represented by QRS-complexes, or in particular, by R-waves.

The signal evaluation unit may further be configured to compute an additional comparative dimension for which M=0 for at least one time interval subset within the set of time intervals.

Preferably, the comparative dimension according to the presented device is computed by generation of at least a difference, a sum, a ratio, a product, a mean value, a deviation, or a variance.

Preferably, the signal evaluation unit is configured to consider all computed comparative dimensions with equal N within the set of time intervals as a group, and to generate a count for each group of those comparative dimensions which fulfill at least one instability criterion.

The signal evaluation unit can further be configured to regard the set of time intervals as irregular when at least one calculated count exceeds at least one threshold, or when all calculated counts exceed at least one threshold.

The evaluation unit can also configured to recognize a pathological state of the heart activity, when a count of consecutive sets of time intervals which are regarded as irregular exceeds a value C, and/or when within a totality Z of sets of time intervals, the count of consecutive sets of time intervals which are regarded as irregular exceeds the value C.

Preferably, the signal evaluation unit is further configured to terminate recognition of a pathological state of the heart activity when a count of consecutive sets of time intervals which are regarded as not irregular exceeds a value D, and/or when within a totality E of sets of time intervals, the count of consecutive sets of time intervals which are regarded as not irregular exceeds the value D.

For instance, recognition of a pathological heart activity state can include marking the respective ECG data as being indicative of a cardiac arrhythmia, which can typically be identified on the ECG by irregular ventricular activity, for example AF or atrial flutter.

The instability criterion can be regarded as fulfilled when the comparative dimension exceeds a limit. The limit can also be calculated dynamically according to the computed comparative dimensions.

The device may include a telemetry module for wireless communication, e.g., via radio frequency (RF) fields, electric fields, and/or magnetic fields. For example, the device may perform wireless data transmission with a remote monitoring system, including an external device which may process the data from the cardiac implant and transmit the data to a further remote system, as for instance a clinical data center. In the remote system, the data from the cardiac device may be stored, post-processed, analyzed and monitored over a longer period of time.

Preferably, there may be a time period of the detection during which rhythms due to premature ventricular contractions are considered, and after which regularity is not used to exclude an arrhythmia episode such as AF. As a specific example, the detection may be used in the first 5 minutes of AF detection in order to avoid triggering of an AF episode by arrhythmias due to premature ventricular contractions in the beginning. Once an AF episode exceeds 5 minutes in duration, the detection may be disabled to avoid discarding or neglecting a long true AF episode due to the presence of premature ventricular contractions in the middle of that episode.

Moreover the invention can be used to filter out periodic rhythms, such as rhythms due to premature ventricular contractions from ECG data. The corresponding ECG data may be stored and/or transferred to external systems to be reviewed by physicians.

DESCRIPTION OF THE DRAWINGS

The foregoing aspects, features and advantages of the invention will be more apparent from the following description in conjunction with the drawings, wherein.

DETAILED DESCRIPTION OF EXEMPLARY VERSIONS OF THE INVENTION

The following description is of the best mode presently contemplated for carrying out at least one version of the invention. This description is not to be taken in a limiting sense, but is made merely for the purpose of describing the general principles of the invention. The scope of rights in the invention should be determined with reference to the claims.

Figure 1:
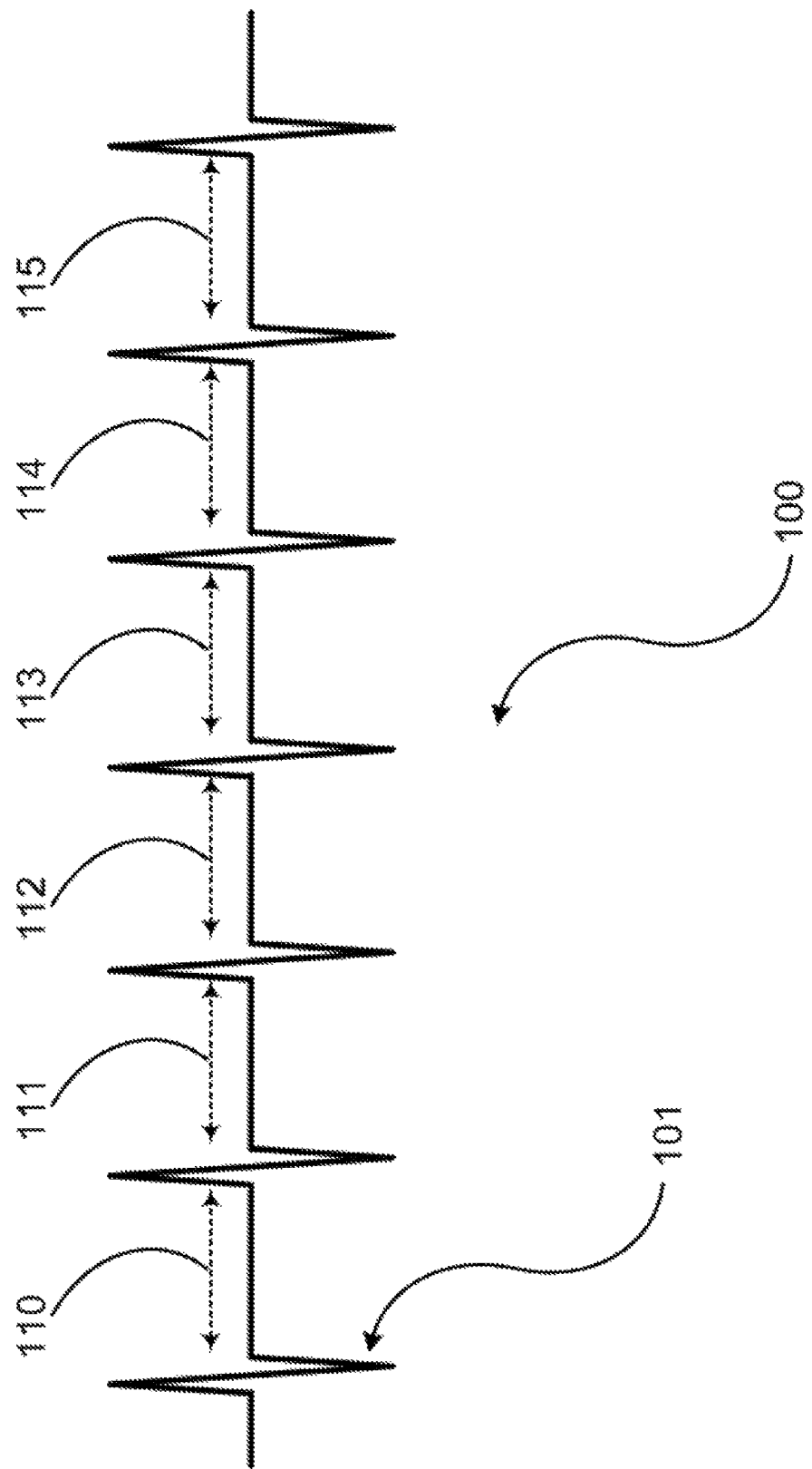
FIG. 1 schematically depicts a signal obtained via ECG data from a heart with regular heart rate.

FIGS. 1 to 5 show schematic examples of different ECG signals 100, 200, 300, 400 and 500 with portions of the signal 101 representing ventricular activity. An ECG signal is either measured by a heart activity monitoring device, or generated from recorded ECG data. FIG. 1 schematically depicts an exemplary ECG signal 100 of a heart with a regular heart rate. The invention may detect portions of the ECG signal 101 representing ventricular activity, for instance QRS complexes or R-waves. Those portions of the signal 101 can be determined using appropriate signal processing and analysis techniques, for example, via amplitude threshold measurement, analysis of the signal slope, and/or other techniques. Moreover, time intervals 110 . . . 115 are measured between each of two ventricular portions of the signal 101.

Each time interval within a set of time intervals is evaluated, wherein the set of time intervals (hereafter referred to as the "set") includes at least three time intervals. The evaluation is performed via computing a comparative dimension (hereafter referred to as the "CD") which represents similarity (or conversely, the difference) in the interval length between the time intervals of a time interval subset (hereafter referred to as the "subset"). A comparative dimension CD can be computed by generating a difference, a sum, a ratio, a product, a mean value, a deviation, a variance, or another mathematical or statistical quantity, between intervals. A subset includes at least two time intervals, and a fixed number of N time intervals lies between each of two time intervals of the subset, wherein preferably N≥1. However, for a set, an additional CD can be computed for at least one subset for which N=0; as will be seen below, this is not as useful because calculating CD for N=0 essentially represents beat-to-beat variations, and thus does not significantly assist with screening for bigeminy, trigeminy, and other periodic premature events.

Within the set of time intervals, all computed CD with equal N are considered as a group, and for each group, a count (hereafter referred to as "$CNum_N$") is calculated for those CD which fulfill at least one instability criterion, for example when the CD exceeds a limit value. Different instability criteria for CD may be applied depending on the conditions under which the invention will operate. The instability criteria can be chosen according to the type of CD, and the required specificity and/or sensitivity for the arrhythmia detection. If a CD is chosen, for example, as the difference value between two time intervals, a high difference value would imply that a change in the rate of ventricular activity has occurred. In that case, it may be appropriate to use a threshold value as an instability criterion. If a CD is chosen, for example, as a mean value of at least two intervals, it may be appropriate to use a reference value as an instability criterion. Such a reference value may be generated dynamically, for example, from previously computed mean values.

The set may be regarded as irregular when at least one $CNum_N$ exceeds at least one threshold, or when all $CNum_N$ exceed at least one threshold. $CNum_N$ can be used to evaluate ECG data regarding arrhythmias, for example, AF. As a practical example, at least a part of the ECG data may be determined to be indicative of AF when some number of consecutive sets of time intervals which are irregular due to their $CNum_N$ exceeds a value A. Alternatively, at least a part of the ECG data may be determined to be indicative of AF when within X sets, the count of consecutive sets of time intervals which are regarded as irregular due to their $CNum_N$ exceeds the value A. Conversely, an AF determination can be removed from ECG data when a count of consecutive sets of non-irregular time intervals exceeds a value B, and/or when within Y sets, the count of consecutive sets which are regarded as non-irregular exceeds the value B. An appropriate threshold for $CNum_N$ can be determined according to the required specificity and/or sensitivity of the arrhythmia detection.

The total number of computable comparative dimensions (CDs) for one set of time intervals depends on:

1. The total number of time intervals within a set;
2. The value(s) chosen for N; and
3. The number of time intervals within a subset.

Following are exemplary applications of the invention for the different ECG signals in FIGS. 1-5. The examples use N=0 . . . 3, and two time intervals within a subset, but different numbers for N, and/or different numbers of time intervals within a subset, may be chosen. The comparative dimension CD is computed as the difference of two time interval lengths. The instability criterion for CD is assumed to be fulfilled when CD is not zero. This instability criterion is chosen for sake of simplicity and clarity, but a different one might be used, with the choice of a suitable instability criterion depending on the nature of the CD and other parameters of the ECG signal analysis. The count $CNum_N$ represents the number of CD which are not zero for the group of CDs with the same N in a set. For all examples:

1. The comparative dimensions CDs are denoted as $CD_{N,i}$ according to the corresponding N and subset number i within a sequence of subsets.
2. Subsets are denoted as $S_{N,i}$ according to the corresponding N and subset number i.
3. The counts CNums are denoted as $CNum_N$ according to the corresponding N.

The ECG signal 100 in FIG. 1 shows an exemplary ECG signal with six time intervals 110 . . . 115 having the same length. If it is assumed that the six time intervals form a set, the following parameters can be computed:

With N=0, five different subsets $S_{0,i}$ can be formed consisting of:

$S_{0,1}$: 110 and 111;
$S_{0,2}$: 111 and 112;
$S_{0,3}$: 112 and 113;
$S_{0,4}$: 113 and 114.
$S_{0,5}$: 114 and 115;
All $CD_{0,i}$=0; $CNum_0$=0.

With N=1, four different subsets $S_{1,i}$ can be formed consisting of:

$S_{1,1}$: 110 and 112;
$S_{1,2}$: 111 and 113;
$S_{1,3}$: 112 and 114;
$S_{1,4}$: 113 and 115.

All $CD_{1,i}$=0; $CNum_1$=0.

With N=2, three different subsets $S_{2,i}$ can be formed consisting of:

$S_{2,1}$: 110 and 113;
$S_{2,2}$: 111 and 114;
$S_{2,3}$: 112 and 115.

All $CD_{2,i}$=0; $CNum_2$=0.

With N=3, two different subsets $S_{3,i}$ can be formed consisting of:

$S_{3,1}$: 110 and 114;
$S_{3,2}$: 111 and 115.

All $CD_{3,i}$=0; $CNum_3$=0.

All $CD_{N,i}$ and $CNum_N$ for the ECG signal in FIG. 1 are zero, meaning that CD does not fulfill the instability criterion. Therefore, the set (the six time intervals) shown in FIG. 1 is not regarded as irregular.

Figure 2:
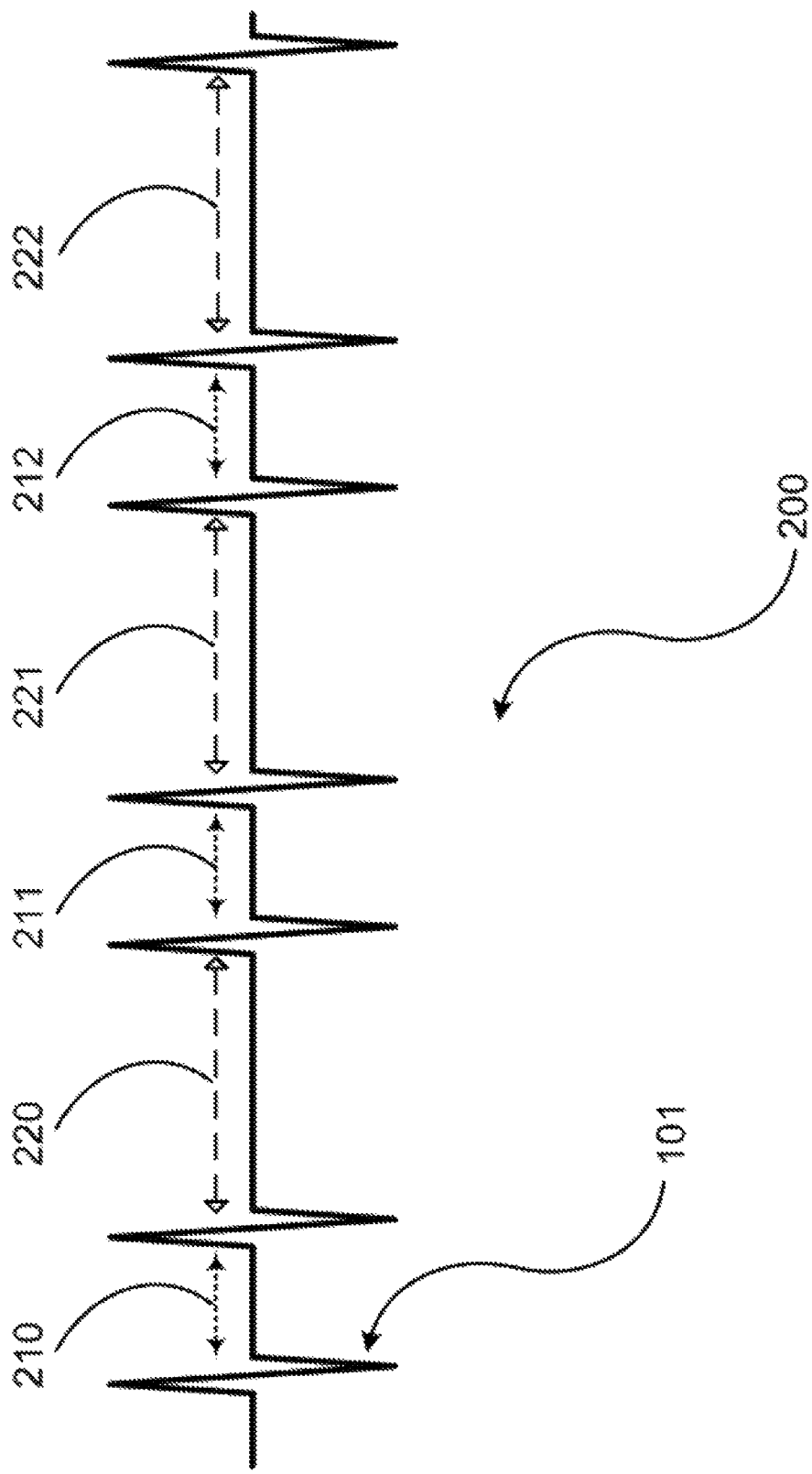
FIG. 2 schematically depicts an exemplary ECG from a heart showing bigeminus beats.

FIG. 2 depicts an exemplary ECG signal 200 with six time intervals, wherein intervals 210, 211, 212 have the same length, and intervals 220, 221, 222 have the same length. The signal represents a schematic example ECG which shows the symptoms of bigeminy arrhythmia, provides all subsets $S_{N,i}$, comparative dimensions $CD_{N,i}$, and count of nonzero comparative dimensions $CNum_N$ for N=0 . . . 3, assuming every $S_{N,i}$ includes two time intervals:

TABLE 1

| N | $S_{N,i}$ (reference signs) | $CD_{N,i}$ (0 or not 0) | $CNum_N$ |
|---|---|---|---|
| 0 | $S_{0,1}$: 210 and 220 | $CD_{0,1}$ = not 0 | $CNum_0$ = 5 |
|   | $S_{0,2}$: 220 and 211 | $CD_{0,2}$ = not 0 |   |
|   | $S_{0,3}$: 211 and 221 | $CD_{0,3}$ = not 0 |   |
|   | $S_{0,4}$: 221 and 212 | $CD_{0,4}$ = not 0 |   |
|   | $S_{0,5}$: 212 and 222 | $CD_{0,5}$ = not 0 |   |
| 1 | $S_{1,1}$: 210 and 211 | $CD_{1,1}$ = 0 | $CNum_1$ = 0 |
|   | $S_{1,2}$: 220 and 221 | $CD_{1,2}$ = 0 |   |
|   | $S_{1,3}$: 211 and 212 | $CD_{1,3}$ = 0 |   |
|   | $S_{1,4}$: 221 and 222 | $CD_{1,4}$ = 0 |   |
| 2 | $S_{2,1}$: 210 and 221 | $CD_{2,1}$ = not 0 | $CNum_2$ = 3 |
|   | $S_{2,2}$: 220 and 212 | $CD_{2,2}$ = not 0 |   |
|   | $S_{2,3}$: 211 and 222 | $CD_{2,3}$ = not 0 |   |
| 3 | $S_{3,1}$: 210 and 212 | $CD_{3,1}$ = 0 | $CNum_2$ = 0 |
|   | $S_{3,2}$: 220 and 222 | $CD_{3,2}$ = 0 |   |

$CNum_N$=0 is an indication for the example that a regularity is detected. In FIG. 2, $CNum_N$=0 has been computed for N=1 and N=3, meaning that a bigeminy structure has been detected and that the set may be regarded as not irregular.

Figure 3:
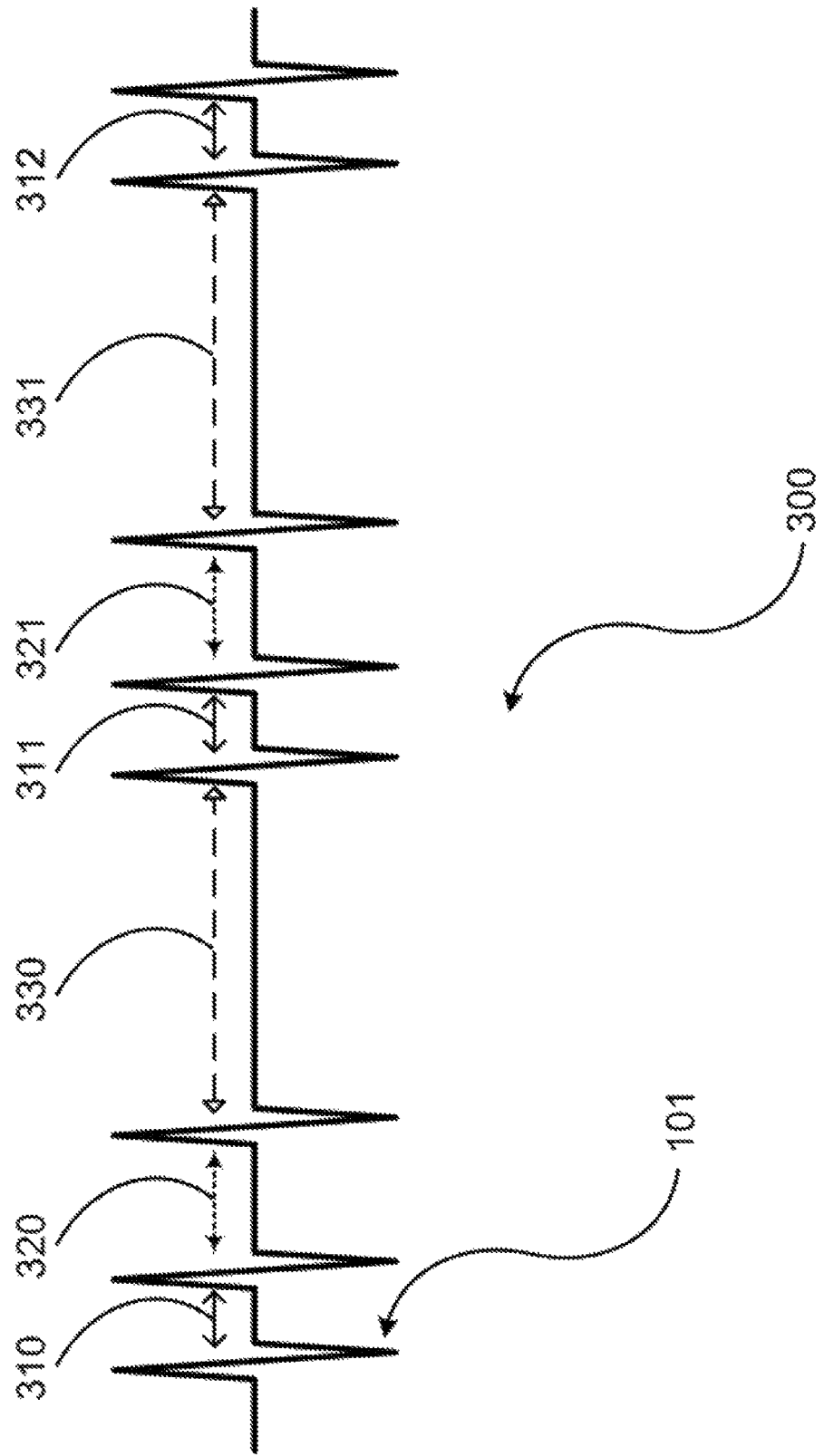
FIG. 3 schematically depicts an exemplary ECG from a heart showing trigeminus beats.

FIG. 3 depicts an exemplary ECG signal 300 with seven time intervals, wherein intervals 310, 311, and 312 have the same length, intervals 320 and 321 have the same length, and intervals 330 and 331 have the same length. The ECG signal 300 shows the symptoms of trigeminy arrhythmia, provides all $S_{N,i}$, $CD_{N,i}$, and $CNum_N$ for N=0 . . . 3, assuming every $S_{N,i}$ includes two time intervals:

TABLE 2

| N | $S_{N,i}$ (reference signs) | $CD_{N,i}$ (0 or not 0) | $CNum_N$ |
|---|---|---|---|
| 0 | $S_{0,1}$: 310 and 320 | $CD_{0,1}$ = not 0 | $CNum_0$ = 6 |
|   | $S_{0,2}$: 320 and 330 | $CD_{0,2}$ = not 0 |   |
|   | $S_{0,3}$: 330 and 311 | $CD_{0,3}$ = not 0 |   |

TABLE 2-continued

| N | $S_{N,i}$ (reference signs) | $CD_{N,i}$ (0 or not 0) | $CNum_N$ |
|---|---|---|---|
|   | $S_{0,4}$: 311 and 321 | $CD_{0,4}$ = not 0 |   |
|   | $S_{0,5}$: 321 and 331 | $CD_{0,5}$ = not 0 |   |
|   | $S_{0,6}$: 331 and 312 | $CD_{0,6}$ = not 0 |   |
| 1 | $S_{1,1}$: 310 and 330 | $CD_{1,1}$ = not 0 | $CNum_1$ = 5 |
|   | $S_{1,2}$: 320 and 311 | $CD_{1,2}$ = not 0 |   |
|   | $S_{1,3}$: 330 and 321 | $CD_{1,3}$ = not 0 |   |
|   | $S_{1,4}$: 311 and 331 | $CD_{1,4}$ = not 0 |   |
|   | $S_{1,5}$: 321 and 312 | $CD_{1,5}$ = not 0 |   |
| 2 | $S_{2,1}$: 310 and 311 | $CD_{2,1}$ = 0 | $CNum_2$ = 0 |
|   | $S_{2,2}$: 320 and 321 | $CD_{2,2}$ = 0 |   |
|   | $S_{2,3}$: 330 and 331 | $CD_{2,3}$ = 0 |   |
|   | $S_{2,4}$: 311 and 312 | $CD_{2,4}$ = 0 |   |
| 3 | $S_{3,1}$: 310 and 321 | $CD_{3,1}$ = not 0 | $CNum_2$ = 3 |
|   | $S_{3,2}$: 320 and 331 | $CD_{3,2}$ = not 0 |   |
|   | $S_{3,3}$: 330 and 312 | $CD_{3,3}$ = not 0 |   |

$CNum_N$=0 indicates regularity is detected. In FIG. 3, $CNum_N$=0 has been computed for N=2, indicating detection of a trigeminus structure, and that the set of intervals need not be regarded as irregular.

Figure 4:
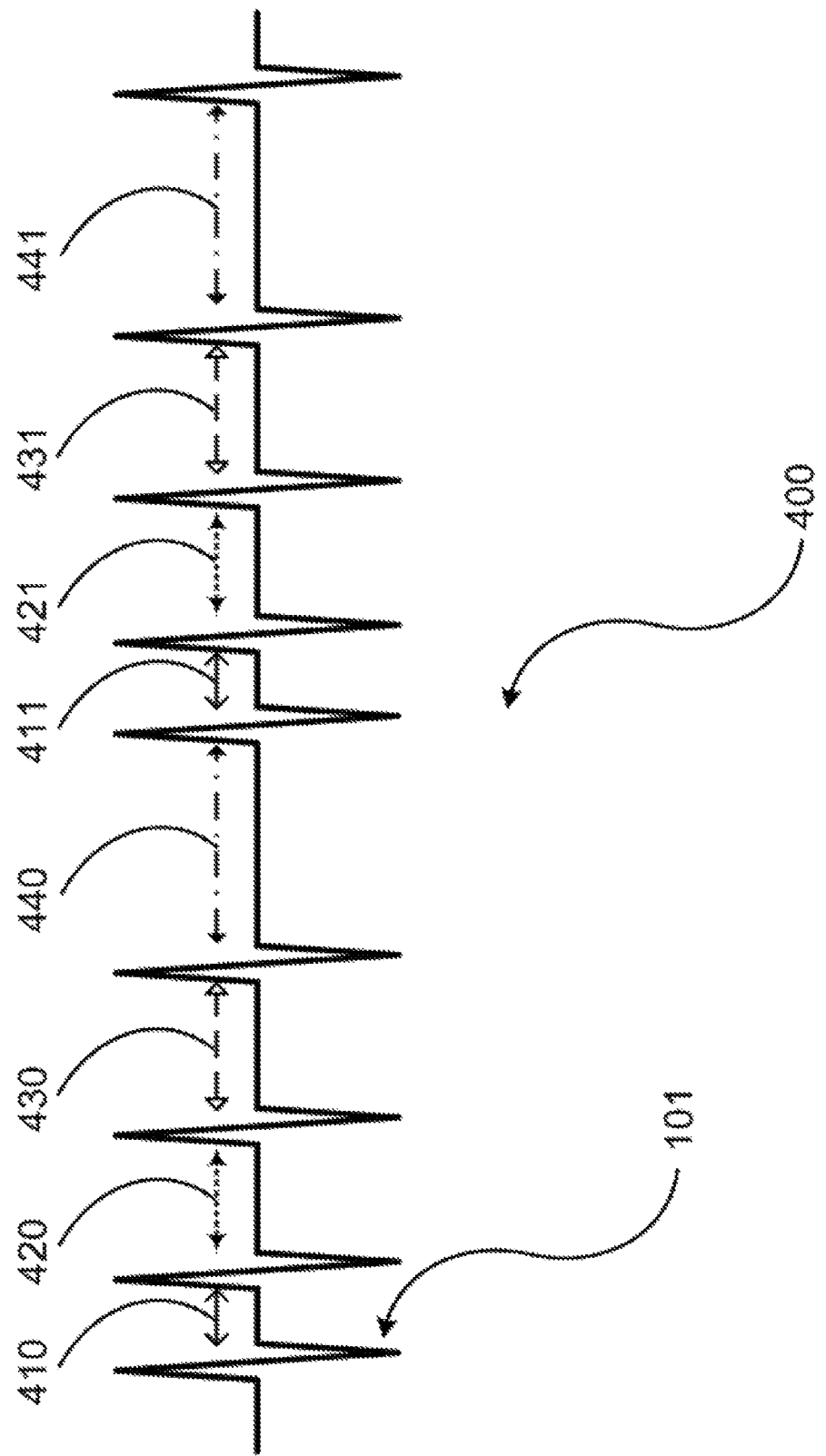
FIG. 4 schematically depicts an exemplary ECG from a heart showing quadrigeminus beats.

FIG. 4 depicts an exemplary ECG signal 400 with eight time intervals, wherein intervals 410 and 411, intervals 420 and 421, intervals 430 and 431, and intervals 440 and 441 have the same length. The ECG signal 400 shows the symptoms of quadrigeminus arrhythmia, provides all $S_{N,i}$, $CD_{N,i}$, and $CNum_N$ for N=0 . . . 3, assuming every $S_{N,i}$ includes two time intervals:

TABLE 3

| N | $S_{N,i}$ (reference signs) | $CD_{N,i}$ (0 or not 0) | $CNum_N$ |
|---|---|---|---|
| 0 | $S_{0,1}$: 410 and 420 | $CD_{0,1}$ = not 0 | $CNum_0$ = 7 |
|   | $S_{0,2}$: 420 and 430 | $CD_{0,2}$ = not 0 |   |
|   | $S_{0,3}$: 430 and 440 | $CD_{0,3}$ = not 0 |   |
|   | $S_{0,4}$: 440 and 411 | $CD_{0,4}$ = not 0 |   |
|   | $S_{0,5}$: 411 and 421 | $CD_{0,5}$ = not 0 |   |
|   | $S_{0,6}$: 421 and 431 | $CD_{0,6}$ = not 0 |   |
|   | $S_{0,7}$: 431 and 441 | $CD_{0,7}$ = not 0 |   |
| 1 | $S_{1,1}$: 410 and 430 | $CD_{1,1}$ = not 0 | $CNum_1$ = 6 |
|   | $S_{1,2}$: 420 and 440 | $CD_{1,2}$ = not 0 |   |
|   | $S_{1,3}$: 430 and 411 | $CD_{1,3}$ = not 0 |   |
|   | $S_{1,4}$: 440 and 421 | $CD_{1,4}$ = not 0 |   |
|   | $S_{1,5}$: 411 and 431 | $CD_{1,5}$ = not 0 |   |
|   | $S_{1,6}$: 421 and 441 | $CD_{1,6}$ = not 0 |   |
| 2 | $S_{2,1}$: 410 and 440 | $CD_{2,1}$ = not 0 | $CNum_2$ = 5 |
|   | $S_{2,2}$: 420 and 411 | $CD_{2,2}$ = not 0 |   |
|   | $S_{2,3}$: 430 and 421 | $CD_{2,3}$ = not 0 |   |
|   | $S_{2,4}$: 440 and 431 | $CD_{2,4}$ = not 0 |   |
|   | $S_{2,5}$: 411 and 441 | $CD_{2,5}$ = not 0 |   |
| 3 | $S_{3,1}$: 410 and 411 | $CD_{3,1}$ = 0 | $CNum_2$ = 0 |
|   | $S_{3,2}$: 420 and 421 | $CD_{3,2}$ = 0 |   |
|   | $S_{3,3}$: 430 and 431 | $CD_{3,3}$ = 0 |   |
|   | $S_{3,4}$: 440 and 441 | $CD_{3,4}$ = 0 |   |

$CNum_N$=0 indicates regularity is detected. In FIG. 4, $CNum_N$=0 has been computed for N=3, indicating detection of a quadrigeminus structure, and that the set of intervals need not be regarded as irregular.

Figure 5:
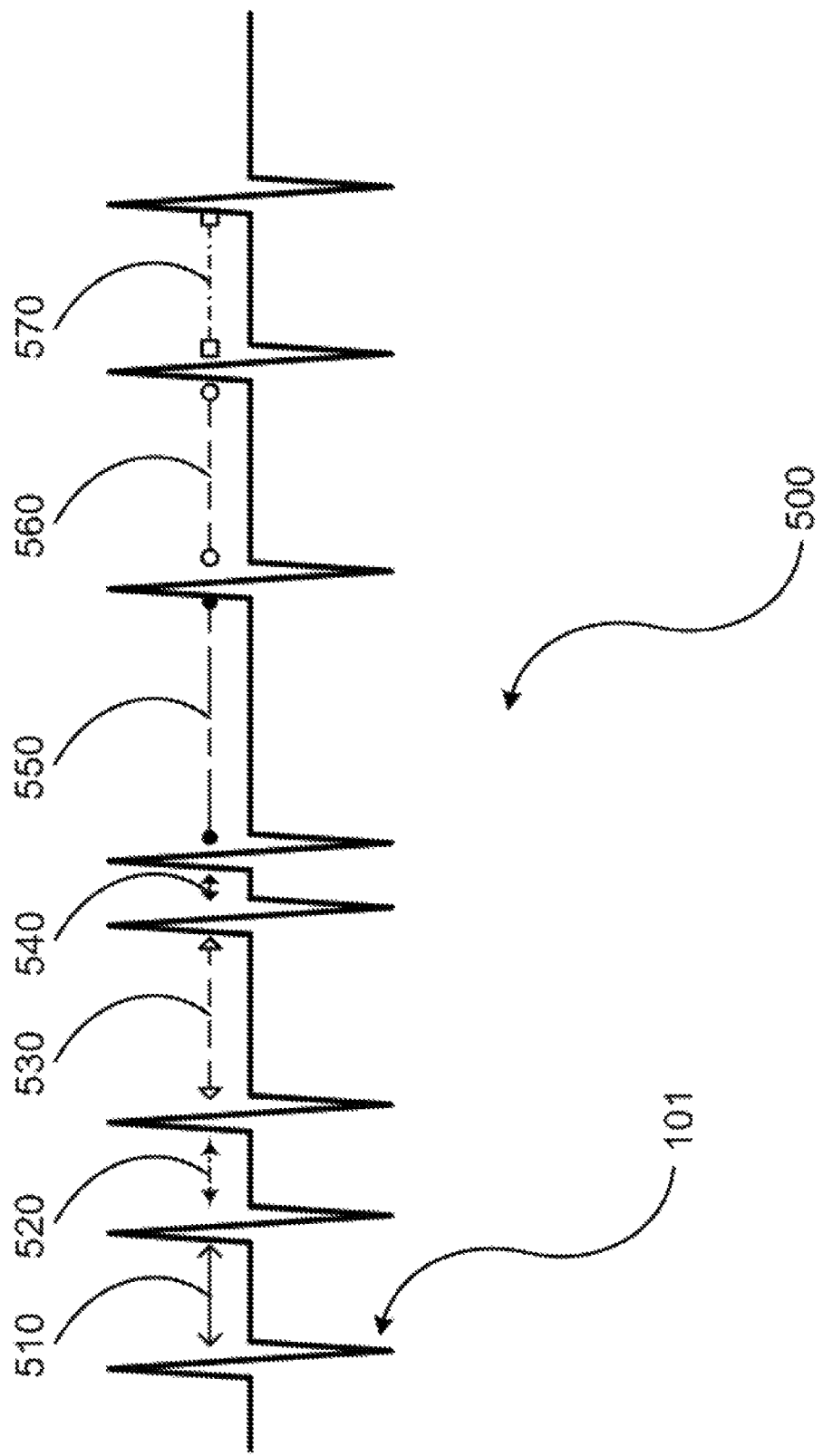
FIG. 5 schematically depicts an exemplary ECG from a heart showing irregularities, such as for the indication of AF.

FIG. 5 depicts an exemplary ECG signal 500 with seven time intervals, wherein all time intervals have different lengths. The ECG signal 500 shows the symptoms of an arrhythmia, more particularly AF, provides all $S_{N,i}$, $CD_{N,i}$, and $CNum_N$ for N=0 . . . 3, and assuming that every $S_{N,i}$ includes two time intervals:

TABLE 4

| N | $S_{N,i}$ (reference signs) | $CD_{N,i}$ (0 or not 0) | $CNum_N$ |
|---|---|---|---|
| 0 | $S_{0,1}$: 510 and 520 | $CD_{0,1}$ = not 0 | $CNum_0$ = 6 |
|   | $S_{0,2}$: 520 and 530 | $CD_{0,2}$ = not 0 | |
|   | $S_{0,3}$: 530 and 540 | $CD_{0,3}$ = not 0 | |
|   | $S_{0,4}$: 540 and 550 | $CD_{0,4}$ = not 0 | |
|   | $S_{0,5}$: 550 and 560 | $CD_{0,5}$ = not 0 | |
|   | $S_{0,6}$: 560 and 570 | $CD_{0,6}$ = not 0 | |
| 1 | $S_{1,1}$: 510 and 530 | $CD_{1,1}$ = not 0 | $CNum_1$ = 5 |
|   | $S_{1,2}$: 520 and 540 | $CD_{1,2}$ = not 0 | |
|   | $S_{1,3}$: 530 and 550 | $CD_{1,3}$ = not 0 | |
|   | $S_{1,4}$: 540 and 560 | $CD_{1,4}$ = not 0 | |
|   | $S_{1,5}$: 550 and 570 | $CD_{1,5}$ = not 0 | |
| 2 | $S_{2,1}$: 510 and 540 | $CD_{2,1}$ = not 0 | $CNum_2$ = 4 |
|   | $S_{2,2}$: 520 and 550 | $CD_{2,2}$ = not 0 | |
|   | $S_{2,3}$: 530 and 560 | $CD_{2,3}$ = not 0 | |
|   | $S_{2,4}$: 540 and 570 | $CD_{2,4}$ = not 0 | |
| 3 | $S_{3,1}$: 510 and 550 | $CD_{3,1}$ = not 0 | $CNum_2$ = 3 |
|   | $S_{3,2}$: 520 and 560 | $CD_{3,2}$ = not 0 | |
|   | $S_{3,3}$: 530 and 570 | $CD_{3,3}$ = not 0 | |

$CNum_N=0$ indicates regularity is detected. In FIG. 5, $CNum_N=0$ is not detected for any N, indicating detection of an irregularity (an arrhythmia). A quality measure may be assigned to at least a part of the ECG data—for example, the set of time intervals in FIG. 5 may be tagged with an AF indicator—where parameters such as those in Table 4 are present.

Figure 6:
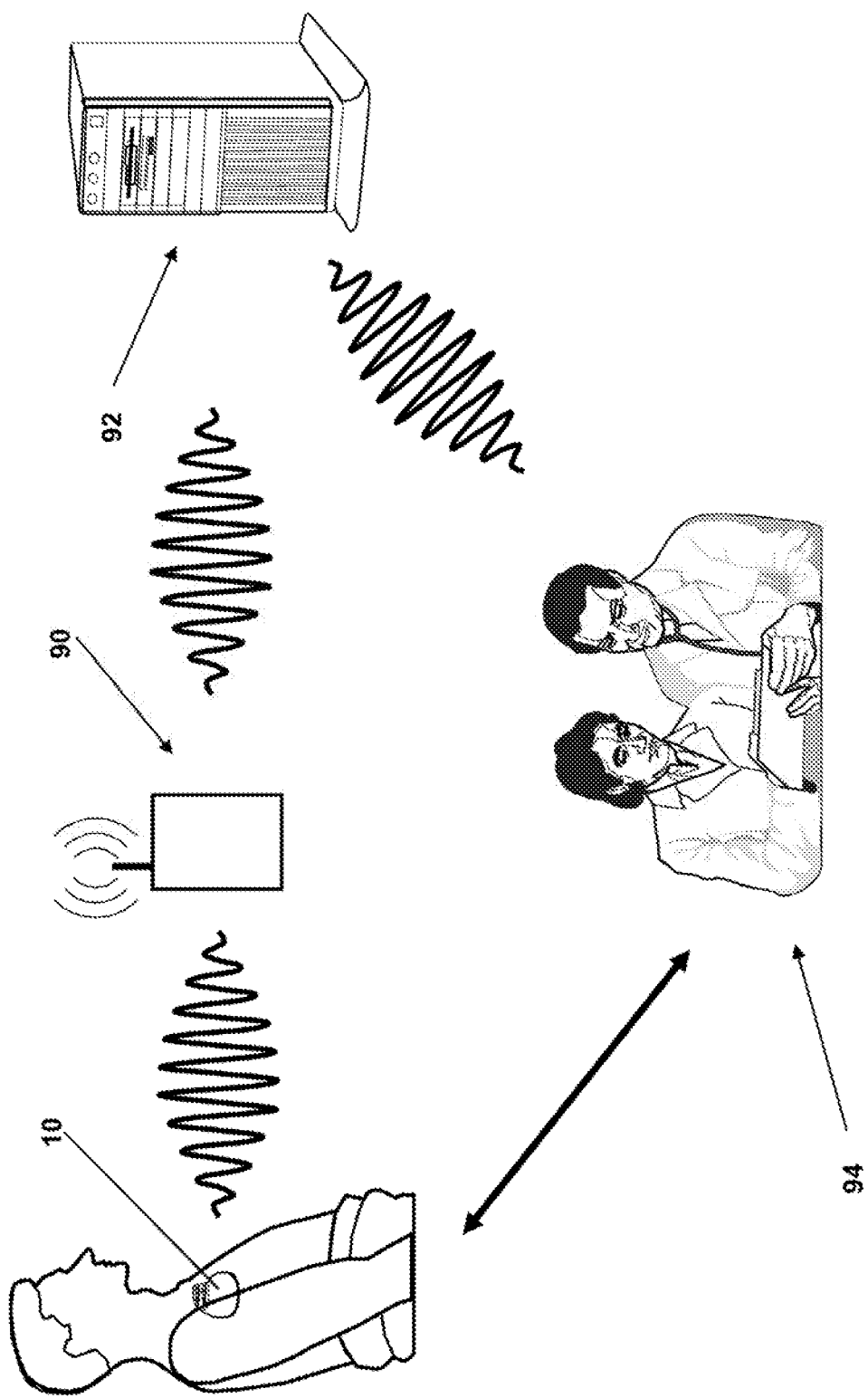
FIG. 6 shows an exemplary version of the invention incorporated within a heart stimulator and a remote monitoring system.

The invention may be incorporated into a heart monitor such as that exemplified in FIG. 6, which depicts a remote monitoring system having an implantable heart monitor or stimulator 10, an external device 90, and a central data server 92 of a central service center. The external device 90 allows (preferably wireless) data communication between the implantable heart monitor/stimulator 10 and the central server 92.

Figure 7:
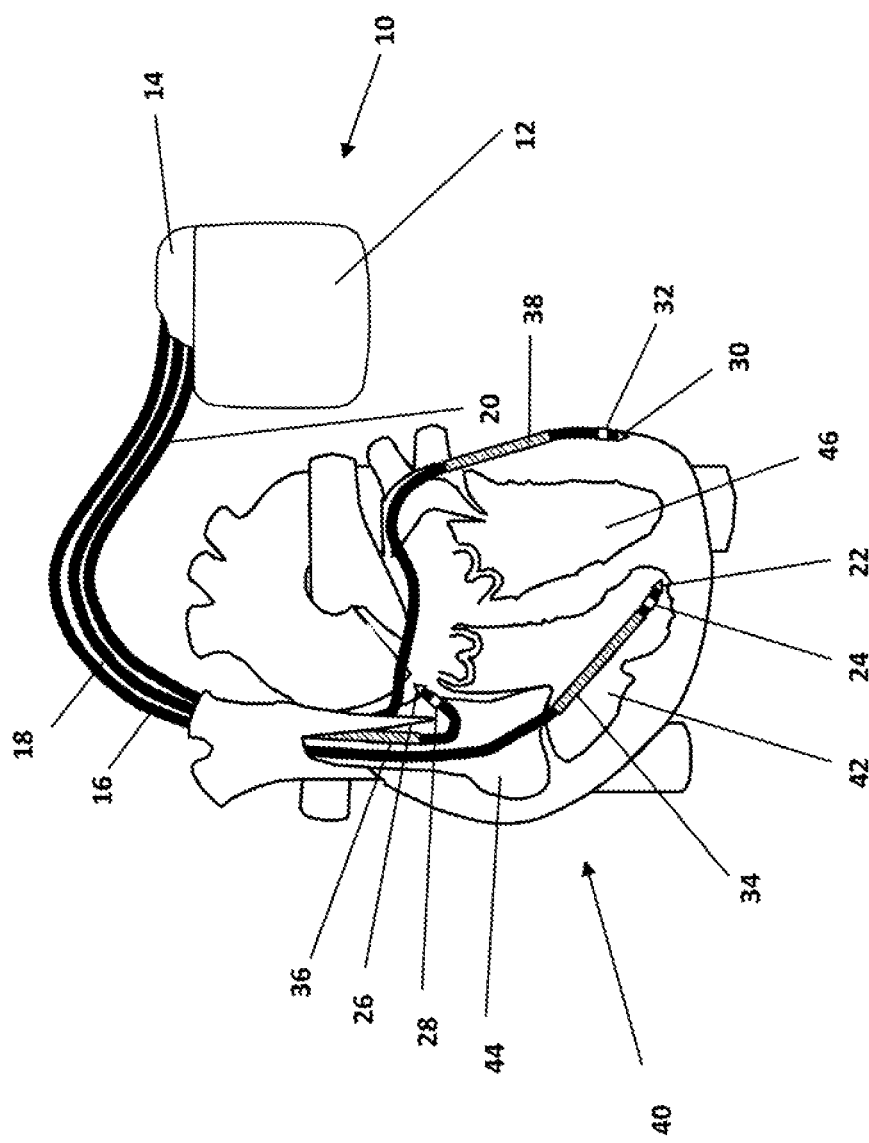
FIG. 7 shows an exemplary version of the invention incorporated within a heart stimulator connected to electrode leads.

FIG. 7 illustrates an exemplary heart stimulator 10 into which the invention may be incorporated, wherein the heart stimulator 10 is connected to electrode leads 16, 18, and 20 placed in a heart. The heart stimulator 10 includes a housing or case 12 having a header 14 from which a right ventricular electrode lead 16, a right atrial electrode lead 18, and a left ventricular electrode lead 20 extend. (However, the invention can also be provided in leadless heart monitors, e.g., where electrodes are situated on the housing/case.) The right atrial electrode lead 18 may include one or more of a distal right atrial tip electrode 26 (RA-tip), a proximal right atrial ring electrode 28 (RA-ring), and/or a superior vena cava coil electrode 36 (SVC-coil), which preferably has a large surface area. The right ventricular electrode lead 16 may include one or more of a distal right ventricular tip electrode 22 (RV-tip), a proximal right ventricular ring electrode 24 (RV-ring), and/or a right ventricular defibrillation coil electrode 34 (RV-coil), which preferably has a large surface area. The left ventricular (LV) lead may include one or more of a distal left ventricular tip electrode 30 (LV-tip), a proximal left ventricular ring electrode 32 (LV-ring), and/or a defibrillation coil electrode 38 (LV-coil), which preferably has a large surface area. As seen in FIG. 7, the left ventricular electrode lead 20 may pass through the coronary sinus of heart 40. Each electrode and shock coil of electrode leads 16, 18, and 20 may be separately connected to an electric circuit enclosed within the case 12 of the heart stimulator 10 by way of plug electrical contacts (not shown) at the proximal end of each electrode lead 16, 18, 20 and corresponding contacts (not shown) in header 14 of heart stimulator 10.

Figure 8:
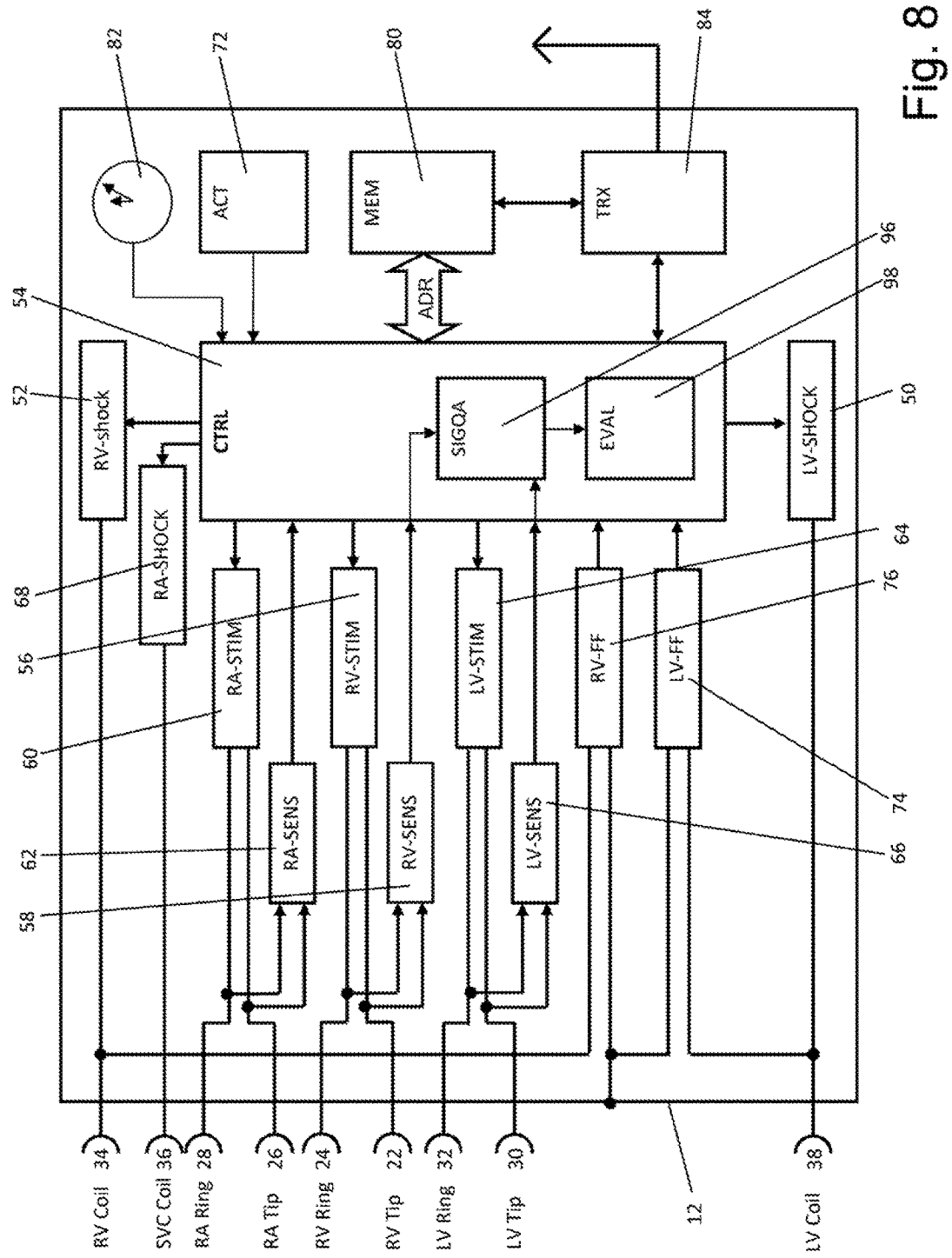
FIG. 8 depicts a schematic block diagram of components of the heart stimulator of FIG. 7.

FIG. 8 depicts a schematic block diagram of components of the heart stimulator 10 of to FIG. 7. The superior vena cava coil electrode (SVC-coil) 36 may be connected to a right atrial shock generator 68 controlled by a control unit 54 of heart stimulator 10. The right atrial tip electrode 26 and right atrial ring, electrode 28 may both be connected to a right atrial stimulation pulse generator 60 and a right atrial sensing stage 62, which may both be connected to the control unit 54. The right atrial stimulation pulse generator 60 may generate atrial stimulation pulses of sufficient strength to cause an excitation of the atrial myocardium by an electrical pulse delivered via the right atrial tip electrode 26 and the right atrial ring electrode 28. Preferably, the right atrial stimulation pulse strength may be adapted to the stimulation threshold in the right atrium. The right atrial sensing stage 62 may pick up myocardial potentials indicating an intrinsic atrial excitation, i.e., a natural atrial contraction. When the heart stimulator is in its demand mode, the right atrial sensing stage 62 may trigger stimulation of the right atrium 44 of the heart 40, or inhibit right atrial stimulation pulses if an intrinsic atrial event (intrinsic atrial excitation) is sensed by the right atrial sensing stage 62 prior to expiration of an atrial escape interval.

Similarly, the right ventricular shock coil 34 may be connected to a right ventricular shock generator 52 connected to the control unit 54, and the left ventricular shock coil 38 may be connected to a left ventricular shock generator 50 connected to the control unit 54. The right ventricular ring electrode 24 and right ventricular tip electrode 22 may be connected to a right ventricular stimulation pulse generator 56 and a right ventricular sensing stage 58, which may in turn both be connected to the control unit 54. The right ventricular sensing stage 58 may further be connected to a signal quality analysis unit 96 of the control unit 54, which may determine whether a noise condition (NC) and/or a low signal indication is present for an intrinsic ventricular event sensed by the right ventricular sensing stage 58. The signal quality analysis unit 96 may generate a noise condition and/or low signal indication signal and provide it to a signal evaluation unit 98. When the heart stimulator is in its demand mode, right ventricular stimulation pulses may be delivered in a demand mode to the right ventricle 42 of heart 40 via the right ventricular tip electrode 22, right ventricular ring electrode 24, right ventricular stimulation generator 56, and right ventricular sensing stage 58.

Similar to the foregoing right ventricular components, the left ventricular tip electrode 30 and left ventricular ring electrode 32 may be connected to the left ventricular stimulation pulse generator 64 and the left ventricular sensing stage 66, and to the signal quality analysis to unit 96 of the control unit 54, allowing stimulation of a left ventricle 46 of the heart 40.

The outputs of the ventricular sensing stages 58 and 66, i.e., sense signals including ventricular events, and the outputs of the signal quality analysis unit 96, i.e., noise condition and/or low signal indication signals, may be provided to the evaluation unit 98. The evaluation unit 98 may evaluate the signals by detecting usable intervals in the sense signals in dependence on the noise condition and/or low signal indication signals. Usable intervals may be intervals defined by two consecutive events that do not have a noise condition and/or a low signal indication. The evaluation unit 98 may execute various monitoring and stimulation algorithms in parallel to monitor for specific heart functional and rhythm disorders, e.g., bradycardia, asystole, high ventricular rate, or other heart functional or rhythm disorders, and may also treat the disorder(s), e.g., by stimulating the left ventricle 46 and/or the right ventricle 42 of heart 40. The evaluation unit 98 may determine an average interval duration, and an average rate of events from the useable intervals, and may use these parameters to detect bradycardia, asystole, and/or high ventricular rate. If a functional disorder has been detected, the evaluation unit 98 may execute an alternative monitoring and stimulation algorithm for the specific functional disorder which has been detected. The alternative monitoring and stimulation algorithm may attempt to detect whether the functional disorder was terminated, as by stimulating the left ventricle 46 or right ventricle 42 of the heart 40. The detection of termination, and stimulation adjusted to a particular detected functional disorder, may also be integrated into monitoring and stimulation algorithms.

The control unit 54 may control triggering of, and inhibition of delivery of, stimulation pulses to the right atrium, the right ventricle or the left ventricle. The scheduled delivery of stimulation pulses (if needed) may be controlled by a number of intervals that may at least partly depend on patient hemodynamic demand, which may be sensed using an activity sensor 72 connected to control unit 54. The activity sensor 72 may allow for rate adaptive pacing wherein a pacing rate (the rate of consecutive ventricular stimulation pulses for a duration of consecutive atrial stimulation pulses) may depend on patient physiological demand, which may be sensed by the activity sensor 72.

A dock 82 may allow recording of time-stamped events and signals, allowing synchronous evaluation of signals at a later time.

A far-field right ventricular electrogram recording unit 76 and/or a far-field left ventricular recording unit 74 may be provided to allow composition of a far-field right ventricular electrogram (RV EGM) and/or a far-field left-ventricular electrogram (LV EGM). The far-field right ventricular electrogram recording unit 76 may be connected to a case electrode, i.e., an electrically conducting part of the case 12 of the heart stimulator 10, and to the RV coil electrode 34. The far-field left ventricular recording unit 74 may also be connected to a case electrode, and to the left ventricular coil electrode 38.

The near-field electrogram in the right ventricle 42 may be measured between the RV-tip electrode 22 and RV-ring electrode 24. The far-field electrogram in the light ventricle 42 may be measured between the device housing 12 and the RV-coil electrode 34, or alternatively the RV-ring electrode 24. Likewise, the near-field electrogram in the left ventricle 46 may be measured between the LV-tip electrode 30 and LV-ring electrode 32, and the far-field electrogram may be measured between the device housing 12 and the LV-coil electrode 38, or alternatively the LV-ring electrode 32.

Preferably, the far-field electrogram in the right ventricle 42 and the left ventricle 46 are minimally filtered and have wide bandwidth. Accordingly, the right and left far-field ventricular recording units 76 and 74 may each include a band pass filter with appropriately high bandwidth, e.g., with a lower corner frequency of 4 Hz and high corner frequency of 128 Hz. The near-field electrograms in the right ventricle 42 and the left ventricle 46 may be filtered with narrower bandwidth. Thus, the right ventricular sensing stage 58 and left ventricular sensing stage 66, which may be used to pick up near-field electrograms in the right ventricle 42 and the left ventricle 46, may each include band-pass filters with corner frequencies providing appropriately narrow bandwidth, e.g., with lower corner frequency 18 Hz and high corner frequency 40 Hz.

Both the far-field electrograms and the near-field electrograms may be used to detect events in the signals, to determine intervals, and/or to determine rates of events. The signal quality analysis unit 96 may determine whether a noise condition (NC) and/or a low signal indication may be present for an intrinsic event sensed by the sensing stages 58, 66 and/or the far-field ventricular electrogram recording units 74, 76. The corresponding noise condition (NC) and/or low signal indication signal may be provided to the evaluation unit 98. The evaluation unit 98 may evaluate the outputs of the sensing stages 58, 66 and the far-field to ventricular electrogram recording units 74, 76 in dependence on the noise condition (NC) and/or low signal indication signal, i.e., it can determine an average interval duration and an average rate of events from the useable intervals, and use these parameters to detect bradycardia, asystole and/or ventricular rate.

The heart monitor 10 may be an implantable device that functions as a loop recorder and detects QRS complexes using the subcutaneous electrodes 22, 24, 30, 32 as shown in FIG. 7 and FIG. 8. The heart monitor 10 may combine different electrode measurements to create a combined signal, and may then perform QRS detection on the combined signal. The detected QRS events may be classified as ventricular sense events (VS) 102 or as invalid sensed events (VN) 104. A VS 102 may be considered a VN 104 if it has an associated noise condition (NC) or low signal indication.

Numerous modifications and variations of the foregoing exemplary versions of the invention are possible, and alternative versions may include some or all of the features noted above. The invention is not intended to be limited to the versions described, but rather is intended to be limited only by the claims set out below. Thus, the invention encompasses all different versions that fall literally or equivalently within the scope of these claims.

What is claimed is:

1. A method for analyzing heart performance data including the steps of:
    a. detecting points in the ECG data which represent ventricular activity,
    b. measuring time intervals between each two consecutive points in the ECG data which represent ventricular activity,
    c. within a set of the time intervals, computing a comparative dimension for each of two or more time interval subsets wherein:
        (1) each time interval subset includes at least two time intervals, and
        (2) the comparative dimension represents similarity between the interval lengths of the time intervals of the time interval subset.

2. The method of claim 1 wherein for each time interval sub set:
    a. a number N of time intervals are situated between each two time intervals within the time interval subset, wherein N is an integer; and
    b. N≥1.

3. The method of claim 2 further including the step of calculating a count, within each group of comparative dimensions having equal N, of those comparative dimensions which meet a predefined instability criterion.

4. The method of claim 3 further including the step of delivering stimulation to a heart by a heart monitoring device, the stimulation being at least partially dependent on the indication of pathology.

5. The method of claim 3 further including the step of:
    a. comparing each count with a respective threshold, and
    b. identifying the set of time intervals as irregular when either:
        (1) at least one count exceeds a threshold, or
        (2) all counts each exceed a threshold.

6. The method of claim 5:
a. performed by a heart monitoring device, the device including:
   (1) electrodes configured to obtain the ECG data,
   (2) a memory for storing the obtained ECG data, and
   (3) a signal evaluation unit wherein the method is executed,
b. further including the step of adapting stimulation delivered by the device to a heart at least partially in dependence on the indication of pathology.

7. The method of claim 5 further including the step of removing the indication of pathology when a number of consecutive sets of time intervals which are not identified as irregular exceeds a value B.

8. The method of claim 3 wherein the instability criterion is fulfilled when the comparative dimension exceeds a limit.

9. The method of claim 5 further including the step of assigning an indication of pathology to at least a part of the ECG data when a number of consecutive sets of time intervals identified as irregular exceeds a value A.

10. The method of claim 1 wherein each comparative dimension is defined by one of:
a. a difference;
b. a sum;
c. a ratio;
d. a product;
e. a mean value
f. a deviation; or;
g. a variance.

11. The method of claim 1 wherein the set of time intervals includes at least three time intervals.

12. The method of claim 1 performed by a heart monitoring device, the device including:
a. electrodes configured to obtain the ECG data,
b. a memory for storing the obtained ECG data, and
c. a signal evaluation unit wherein the method is executed.

13. A method for analyzing heart performance data including the steps of:
a. determining time intervals between consecutive ventricular events,
b. within a set of the time intervals, computing a comparative dimension for each of two or more time interval subsets wherein:
   (1) each time interval subset includes at least two time intervals,
   (2) within each time interval subset, a number N of time intervals are situated between each two time intervals therein, N being an integer greater than 1,
   (3) the comparative dimension is dependent on the similarity between the interval lengths of the time intervals of the time interval subset,
c. calculating one or more comparative dimension counts, each count having comparative dimensions:
   (1) computed from time interval subsets having equal N, and
   (2) which meet a predefined instability criterion,
d. delivering stimulation to a heart, the stimulation being at least partially dependent on the counts.

14. The method of claim 13 wherein each comparative dimension is defined by one of:
a. a difference;
b. a sum;
c. a ratio;
d. a product;
e. a mean value
f. a deviation; or
g. a variance,
between interval lengths.

15. The method of claim 13 further including the steps of:
a. comparing each count with a respective threshold, and
b. changing the stimulation delivered to the heart where a predetermined number of counts exceeds a threshold, the predetermined number being greater than or equal to 1.

16. The method of claim 13 further including the steps of:
a. comparing each count with a respective threshold,
b. identifying the set of time intervals as irregular if a predetermined number of counts exceeds a threshold, the predetermined number of counts being greater than or equal to 1, and
b. changing the stimulation delivered to the heart if a predetermined number of consecutive sets of time intervals identified as irregular exceeds a value A, the predetermined number of consecutive sets being greater than or equal to 2.

17. The method of claim 13 wherein at least three comparative dimension counts are calculated.

18. A heart monitoring device including:
a. electrodes configured to obtain ECG data,
b. a memory for storing the obtained ECG data, and
c. a signal evaluation unit configured to:
   (1) determine time intervals between consecutive ventricular events within the ECG data,
   (2) within a set of the time intervals, compute a comparative dimension for each of two or more time interval subsets wherein:
      (a) each time interval subset includes two or more time intervals,
      (b) within each time interval subset, a number N of time intervals are situated between each two time intervals therein, wherein N is an integer,
      (c) the comparative dimension is dependent on the similarity between the interval lengths of the time intervals of the time interval subset,
c. calculating one or more comparative dimension counts, each count having comparative dimensions:
   (1) computed from time interval subsets having equal N, and
   (2) which meet a predefined instability criterion,
d. delivering stimulation to a heart, the stimulation being at least partially dependent on the counts.

* * * * *